(12) United States Patent
Mendrok-Edinger et al.

(10) Patent No.: US 11,324,680 B2
(45) Date of Patent: May 10, 2022

(54) TOPICAL COMPOSITIONS

(71) Applicant: DSM IP ASSETS B.V., Heerlen (NL)

(72) Inventors: Christine Mendrok-Edinger, Kaiseraugst (CH); Sebastien Mongiat, Kaiseraugst (CH); Thomas Rudolph, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 28 days.

(21) Appl. No.: 16/628,426

(22) PCT Filed: Jun. 28, 2018

(86) PCT No.: PCT/EP2018/067371
§ 371 (c)(1),
(2) Date: Jan. 3, 2020

(87) PCT Pub. No.: WO2019/007792
PCT Pub. Date: Jan. 10, 2019

(65) Prior Publication Data
US 2020/0155431 A1 May 21, 2020

(30) Foreign Application Priority Data

Jul. 6, 2017 (EP) ..................... 17180071

(51) Int. Cl.
*A61K 8/35* (2006.01)
*A61K 8/37* (2006.01)
*A61K 8/60* (2006.01)
*A61K 9/107* (2006.01)
*A61Q 17/00* (2006.01)
*A61Q 19/00* (2006.01)

(52) U.S. Cl.
CPC ................ *A61K 8/35* (2013.01); *A61K 8/375* (2013.01); *A61K 8/60* (2013.01); *A61K 9/107* (2013.01); *A61Q 17/005* (2013.01); *A61Q 19/00* (2013.01); *A61K 2800/21* (2013.01); *A61K 2800/48* (2013.01)

(58) Field of Classification Search
None
See application file for complete search history.

(56) References Cited

U.S. PATENT DOCUMENTS

| | | |
|---|---|---|
| 2005/0220726 A1 | 10/2005 | Pauly et al. |
| 2010/0286218 A1 | 11/2010 | Berg et al. |
| 2016/0235661 A1 | 8/2016 | Changoer et al. |
| 2016/0367454 A1 | 12/2016 | Katsukura |

FOREIGN PATENT DOCUMENTS

| | | |
|---|---|---|
| EP | 0 221 728 | 5/1987 |
| KR | 10-2014-0062838 | 5/2014 |

OTHER PUBLICATIONS

Bresco et al., "Pathogenic Mechanisms and Host Interactions in *Staphylococcus epidermidis* Device-Related Infection", Front. Microbiol., 8, 2017, pp. 1401. (Year: 2017).*
"Radiance Cycle Natural Glow Face Serum", Mintel, XP-002784090, published Jul. 1, 2011, 6 pages.
"Moisturizing Self-Tanning Silky Gel", Mintel, XP-002784089, published Jun. 1, 2017, 4 pages.
International Search Report for PCT/EP2018/067371 dated Sep. 21, 2018, 4 pages.
Written Opinion of the ISA for PCT/EP2018/067371 dated Sep. 21, 2018, 7 pages.

\* cited by examiner

*Primary Examiner* — Melissa L Fisher
(74) *Attorney, Agent, or Firm* — Nixon & Vanderhye P.C.

(57) ABSTRACT

The present invention relates to topical compositions comprising erythrulose and a caprylate, characterized in that the amount of the caprylate in the composition is 5 higher than the amount of erythrulose.

14 Claims, No Drawings

TOPICAL COMPOSITIONS

This application is the U.S. national phase of International Application No. PCT/EP2018/067371 filed Jun. 28, 2018 which designated the U.S. and claims priority to EP Application No. 17180071.7 filed Jul. 6, 2017, the entire contents of each of which are hereby incorporated by reference.

The present invention relates to topical compositions comprising erythrulose and a caprylate, characterized in that the amount of the caprylate in the composition is higher than the amount of erythrulose.

Surprisingly it has now been found that that mixtures of erythrulose and glyceryl caprylate exhibit a synergistically enhanced antimicrobial activity against fungi and/or bacteria. Thus, the mixture can effectively be used to balance the skin microbiome and overcome adverse effects resulting from microbial overpopulation on the skin as well as support preservation of products such as cosmetic compositions.

Thus, in a first embodiment the present invention relates to topical compositions comprising erythrulose and a caprylate, characterized in that the weight-ratio (w/w) of the caprylate to erythrulose in the composition is >1.

The term caprylate as used herein refers to esters of caprylic acid commonly used in cosmetic applications. Particularly suitable caprylates according to the present invention encompass glyceryl caprylate, coco caprylate as well as sorbitan caprylate. In all embodiments of the present invention glyceryl caprylate is however preferred.

In another embodiment, the invention relates to the use of a mixture of erythrulose and a caprylate as antimicrobial agent such as in particular against *P. acnes* and/or *C. albicans*. In a preferred embodiment, the weight ratio (w/w) of the caprylate to erythrulose in the mixture is >1.

In a further embodiment, the invention relates to a method of killing and/or inhibiting growth of microbial cells, in particular fungal and/or bacterial cells, such as in particular *P. acnes* and/or *C. albicans*, with a mixture of erythrulose and a caprylate. In a preferred embodiment the weight-ratio (w/w) of the caprylate to erythrulose in the mixture is >1.

In another embodiment, the invention relates to a method for killing and/or inhibiting growth of microbial cells, in particular fungal and/or bacterial cells such as in particular *P. acnes* and/or *C. albicans* said method comprising contacting said microbial cells with mixture of erythrulose and a caprylate, preferably in a weight ratio (w/w) of the caprylate to erythrulose of >1 and optionally appreciating the effect.

In all embodiments of the present invention the mixture of erythrulose and a caprylate, preferably glyceryl caprylate with all the definitions and preferences as given herein is preferably used for killing and/or inhibiting the growth of yeasts such as *C. albicans* and/or bacteria such as *P. acne*. Preferably the mixture is used to kill/inhibit the growth of *C. albicans* as here the mixture is particularly effective.

Due to the antimicrobial activity against fungal and/or bacterial cells the mixture of erythrulose and the caprylate, preferably glyceryl caprylate, even more preferably in a weight ratio (w/w) of the caprylate, to erythrulose of >1, is further suitable for the treatment of adverse skin conditions associated with an overpopulation of such fungal and/or bacterial cells by maintaining skin homeostasis and/or improving the health of the skin microbiome.

Thus, the invention also relates to a method of treating the skin and/or the scalp, said method comprising the steps of contacting the skin and/or scalp with a topical composition according to the invention, in particular for maintaining skin homeostasis and/or improving skin microbiome balance.

In a further embodiment, the present invention relates to the use of a topical composition according to the present invention for maintaining skin homeostasis and/or balancing the skin microbiome.

Further suitable uses of the topical compositions according to the present invention encompass pharmaceutical applications. Thus, the topical compositions according to the present invention may be used for the treatment, prevention and/or prophylaxis of any disorder and disease where it is desirable to kill and/or inhibit the growth of fungal and/or bacterial cells such as in particular *P. acnes* and/or *C. albicans*.

As the mixture is particularly suitable to inhibit *C. albicans*, the mixture is also particularly suitable for the preservation of various products.

Thus, in another embodiment, the present invention relates to the use of mixture of erythrulose and a caprylate, preferably glyceryl caprylate, more preferably in a weight ratio (w/w) of the caprylate to erythrulose of >1, for improving preservation, in particular of a product selected from the group of cosmetic compositions, household products, plastics, paper and/or paints compared to the product not containing the mixture and optionally appreciating the effect, by effectively inhibiting the growth of *C. albicans* respectively killing *C. albicans*.

In another embodiment, the invention relates to a method of preventing microbial decay and breakdown, in particular caused by *C. albicans*, of cosmetic and/or pharmaceutical compositions, household products, plastics, paper and/or paints, wherein said method comprises adding to the compositions, products, plastics, papers and/or paints a mixture of erythrulose and a caprylate, preferably glyceryl caprylate, more preferably in a weight ratio (w/w) of the caprylate to erythrulose of >1. In a particular embodiment, the method also encompasses the step of appreciating the result.

In a particular advantageous embodiment, the invention relates to a method of preventing microbial decay and breakdown of cosmetic or pharmaceutical compositions furthermore comprising water and at least one further agent selected from the group consisting of surfactants, emulsifiers, thickeners, and oils as such compositions are particular sensitive to microbial growth.

As the mixture also excerpts a synergistic effect with respect to *P. acnes*, the present invention furthermore relates to the use of a mixture of erythrulose and a caprylate, preferably glyceryl caprylate, more preferably in a weight ratio (w/w) of the caprylate to erythrulose of >1 as anti-acne active compound. In particular, the mixture is suitable for the treatment or prophylaxis of acne which is triggered by P. Acnes.

The term "erythrulose" refers to erythrulose in D- or L-form or as the racemate. Preferably L-(+)-Erythrulose [533-50-6] is used. Erythrulose is e.g. commercially available at DSM Nutritional Products Ltd, Kaiseraugst.

Glyceryl caprylate [26402-26-6] is e.g. commercially available as Dermosoft GMCY at Dr. Straetmann.

The term "antimicrobial activity" (or "antimicrobial effect") as used herein means a capability of killing and/or inhibiting the growth of microbial cells such as fungal or bacterial cells, such as in particular *P. acnes, S. epidermis, C. xerosis, A. brasiliensis, C. albicans, P. aeruginosa, E. coli, M. furfur* and/or *S. aureus*, in particular *P. acnes* and/or *C. albicans*, most in particular *C. albicans*.

In all embodiments of the present invention the topical compositions preferably comprise erythrulose in an amount selected in the range of about 0.005 to 5 wt.-%, more preferably in the range of about 0.01 to 3 wt.-% and most preferably in the range of 0.025 to 2 wt.-%, such as in an amount of 0.04 to 1 wt.-% and particularly advantageous in an amount of 0.04 to 0.75 wt.-%, based on the total weight of the composition. Further suitable ranges are 0.01 to 0.25 wt.-%, 0.05 to 0.25 wt.-%, 0.01 to 0.2 wt.-%, 0.05 to 0.2 wt.-%, 0.05 to 0.15 wt.-%, 0.01 to 0.15 wt.-% 0.05 to 0.1 wt.-% and 0.01 to 0.1 wt.-%

In all embodiments of the present invention the topical compositions preferably comprise the caprylate, preferably glyceryl caprylate in an amount selected in the range of about 0.1 to about 2 wt.-%, preferably in the range of 0.2 to 1.5 wt.-%, most preferably in the range of 0.3 to 1 wt.-%, based on the total weight of the composition. Further suitable ranges are 0.01 to 0.25 wt.-%, 0.05 to 0.25 wt.-%, 0.01 to 0.2 wt.-%, and 0.05 to 0.2 wt.-%.

In all embodiments of the present invention the weight-ratio (w/w) of the caprylate, preferably glyceryl caprylate to erythrulose is preferably >1.5 and more preferably >1.75. Even more advantageously in all embodiments of the present invention the weight ratio (w/w) is selected in the range of 1.25 to 3, such as in the range of 1.5 to 2.5.

To make use of the anti-microbial activity of the combination of erythrulose and a caprylate, preferably glyceryl caprylate, it can be used in a multiplicity of formulations or applications, such as, for example, cosmetic or pharmaceutical compositions, medicinal products or household products.

The use according to the invention of the combination of erythrulose and a caprylate, preferably glyceryl caprylate can take place both in the cosmetic sense as well as in the pharmaceutical sense. A pharmaceutical application is conceivable, for example, in the case of anti-dandruff or anti-acne compositions. In all embodiments of the present invention, the use is however preferably cosmetic (non-therapeutic) such as for maintenance of skin homeostasis and/or balancing the skin microbiome.

The topical compositions according to the present invention are preferably cosmetic or pharmaceutical compositions which are topically applied to mammalian keratinous tissue such as in particular to human skin or the human scalp and hair.

The term "cosmetic composition" as used in the present application refers to cosmetic compositions as defined under the heading "Kosmetika" in Römpp Lexikon Chemie, 10th edition 1997, Georg Thieme Verlag Stuttgart, New York as well as to cosmetic compositions as disclosed in A. Domsch, "Cosmetic Compositions", Verlag für chemische Industrie (ed. H. Ziolkowsky), $4^{th}$ edition, 1992.

The cosmetic or pharmaceutical compositions according to the present invention preferably further comprise a physiologically acceptable medium, that is to say a medium compatible with keratinous substances, such as the skin, mucosa, and keratinous fibers. Preferably, the physiologically acceptable medium is a cosmetically or pharmaceutically acceptable carrier.

The term cosmetically or pharmaceutically acceptable carrier refers to all carriers and/or excipients and/or diluents conventionally used in cosmetic compositions.

The topical compositions according to the present invention are generally prepared by admixing erythrulose and a caprylate, preferably glyceryl caprylate in the amounts indicated herein with a suitable carrier.

The exact amount of carrier will depend upon the actual level of erythrulose and a caprylate, preferably glyceryl caprylate and any other optional ingredients that one of ordinary skill in the art would classify as distinct from the carrier (e.g., other active ingredients).

In an advantageous embodiment, the cosmetic or pharmaceutical compositions according to the present invention comprise from about 50% to about 99%, preferably from about 60% to about 98%, more preferably from about 70% to about 98%, such as in particular from about 80% to about 95% of a carrier, based on the total weight of the cosmetic composition.

In a particular advantageous embodiment, the carrier consists furthermore of at least 40 wt.-%, more preferably of at least 50 wt.-%, most preferably of at least 55 wt.-% of water, such as in particular of about 55 to about 90 wt.-% of water.

The compositions of the invention (including the carrier) may comprise conventional adjuvants and additives, such as preservatives/antioxidants, fatty substances/oils, organic solvents, silicones, thickeners, softeners, emulsifiers, anti-foaming agents, aesthetic components such as fragrances, surfactants, fillers, anionic, cationic, nonionic or amphoteric polymers or mixtures thereof, propellants, acidifying or basifying agents, dyes, colorings/colorants, abrasives, absorbents, chelating agents and/or sequestering agents, essential oils, skin sensates, astringents, pigments or any other ingredients usually formulated into such compositions.

In accordance with the present invention, the compositions according to the invention may also comprise further cosmetically active ingredients conventionally used in cosmetic or pharmaceutical compositions. Exemplary active ingredients encompass skin lightening agents; UV-filters, agents for the treatment of hyperpigmentation; agents for the prevention or reduction of inflammation; firming, moisturizing, soothing, and/or energizing agents as well as agents to improve elasticity and skin barrier.

Examples of cosmetic excipients, diluents, adjuvants, additives as well as active ingredients commonly used in the skin care industry which are suitable for use in the cosmetic compositions of the present invention are for example described in the International Cosmetic Ingredient Dictionary & Handbook by Personal Care Product Council (http://www.personalcarecouncil.org/), accessible by the online INFO BASE (http://online.personalcarecouncil.org/jsp/Home.jsp), without being limited thereto.

The necessary amounts of the active ingredients as well as the excipients, diluents, adjuvants, additives etc. can, based on the desired product form and application, easily be determined by the skilled person. The additional ingredients can either be added to the oily phase, the aqueous phase or separately as deemed appropriate.

The cosmetically active ingredients useful herein can in some instances provide more than one benefit or operate via more than one mode of action.

Of course, one skilled in this art will take care to select the above mentioned optional additional ingredients, adjuvants, diluents and additives and/or their amounts such that the advantageous properties intrinsically associated with the combination in accordance with the invention are not, or not substantially, detrimentally affected by the envisaged addition or additions.

Preferably, the cosmetic or pharmaceutical compositions according to the invention are in the form of a suspension or dispersion in solvents or fatty substances, or alternatively in the form of an emulsion or micro emulsion (in particular of O/W- or W/O-type), PIT-emulsion, nano emulsion, multiple emulsion (e.g. O/W/O- or W/O/W-type), pickering emulsion, hydrogel, lipogel, one- or multiphase solution or vesicular dispersion.

The cosmetic or pharmaceutical compositions in accordance with the invention can be in the form of a liquid, lotion, a thickened lotion, a gel, a cream, a milk, an ointment or a paste.

The cosmetic or pharmaceutical compositions according to the invention have a pH in the range of 3-10, preferably in the range of pH of 3-8, most preferred in the range of pH 3-6.5. The pH is adjusted by methods known to a person skilled in the art, e.g. by using an acid such as a hydroxy acid including glycolic acid, lactic acid, malic acid, citric acid and tartaric acid or a base such as e.g. sodium or potassium hydroxide or ammonium hydroxide as well as mixtures thereof.

Preferably, in the compositions according to the invention citric acid in an amount of at least 0.0001 wt.-%, such as e.g. in an amount of 0.01-1 wt.-%, in particular in an amount of 0.01 to 0.5 wt.-% is used for pH adjustment.

The cosmetic compositions according to the present invention advantageously comprise a preservative. Particular suitable preservatives in all embodiments of the present invention are phenoxyethanol and ethylhexylglycerin as well as mixtures thereof. When present, the preservative is preferably used in an amount of 0.01 to 2 wt.-%, more preferably in an amount of 0.05 to 1.5 wt.-%, most preferably in an amount of 0.1 to 1.0 wt.-%, based on the total weight of the composition.

The cosmetic compositions according to the present invention are in particular skin care preparations, functional preparations and/or hair care preparations such as most in particularly skin or hair care preparations.

Examples of skin care preparations are, in particular, light protective preparations, anti-ageing preparations, preparations for the treatment of photo-ageing, body oils, body lotions, body gels, treatment creams, skin protection ointments, moisturizing preparations such as moisturizing gels or moisturizing sprays, face and/or body moisturizers, as well as skin lightening preparations.

Examples of functional preparations are cosmetic compositions containing active ingredients such as hormone preparations, vitamin preparations, vegetable extract preparations, anti-ageing preparations, and/or antimicrobial (antibacterial or antifungal) preparations without being limited thereto.

Examples hair care preparations which are suitable according to the invention and which may be mentioned are shampoos, hair conditioners (also referred to as hair rinses), hairdressing compositions, hair tonics, hair regenerating compositions, hair lotions, water wave lotions, hair sprays, hair creams, hair gels, hair oils, hair pomades or hair brilliantines. Accordingly, these are always preparations which are applied to the hair and the scalp for a shorter or longer time depending on the actual purpose for which they are used.

If the hair care preparations according to the invention are supplied as shampoos, these can be clear liquids, opaque liquids (with pearly luster effect), in cream form, gel-like or else in powder form or in tablet form, and as aerosols. The surfactant raw materials on which these shampoos are based can be anionic, cationic, nonionic and amphoteric in nature and also be present in combinations of these substances.

Examples of anionic surfactants suitable for the incorporation into the shampoo preparations according to the present invention are $C_{10-20}$ alkyl- and alkylenecarboxylates, alkyl ether carboxylates, fatty alcohol sulfates, fatty alcohol ether sulfates, alkylolamide sulfates and sulfonates, fatty acid alkylolamide polyglycol ether sulfates, alkanesulfonates and hydroxyalkanesulfonates, olefinsulfonates, acyl esters of isothionates, alpha-sulfo fatty acid esters, alkyl benzenesulfonates, alkylphenol glycol ether sulfonates, sulfosuccinates, sulfosuccinic monoesters and diesters, fatty alcohol ether phosphates, protein-fatty acid condensation products, alkyl monoglyceride sulfates and sulfonates, alkyl glyceride ether sulfonates, fatty acid methyltaurides, fatty acid sarcosinates, and sulforicinoleates. These compounds and their mixtures are used in the form of their salts which are soluble in water or dispersible in water, for example the sodium, potassium, magnesium, ammonium, mono-, di- and triethanolammonium and analogous alkylanunonium salts.

Examples of suitable cationic surfactants are quaternary ammonium salts such as di($C_{10}$-$C_{24}$alkyl)dimethylammonium chloride or bromide, preferably di ($C_{12}$-$C_{18}$alkyl)-dimethylammonium chloride or bromide; $C_{10}$-$C_{24}$-alkyldimethylethylammonium chloride or bromide; $C_{10}$-$C_{24}$-alkyltrimethylammonium chloride or bromide, preferably cetyltrimethylammonium chloride or bromide and $C_{20}$-$C_{24}$-alkyltrimethylammonium chloride or bromide; $C_{10}$-$C_{24}$4-alkyldimethylbenzylammonium chloride or bromide, preferably $C_{12}$-$C_{18}$-alkyldime methylbenzylammoniumchloride; N—($C_{12}$-$C_{18}$-alkyl)pyridinium chloride or bromide, preferably N—($C_{12}$-$C_{16}$-alkyl) pyridinium chloride or bromide; N—($C_{12}$-$C_{18}$-alkyl)isoquinolinium chloride, bromide or monoalkyl sulfate; N—($C_{12}$-$C_{18}$-alkyloylcolaminoformylmethyl)pyridinium chloride; N—($C_{12}$-$C_{18}$-alkyl)-N-methylmorpholinium chloride, bromide or monoalkyl sulfate; N—($C_{12}$-$C_{18}$-alkyl)-N-ethylmorpholinium chloride, bromide or monoalkyl sulfate; $C_{16}$-$C_{18}$-alkylpentaoxethylammonium chloride; isobutylphenoxyethoxyethyldimethyl-benzylammonium chloride; salts of N,N-diethylaminoethylstearylamide and oleylamide with hydrochloric acid, acetic acid, lactic acid, citric acid, phosphoric acid; N-acylamidoethyl-N,N-diethyl-N-methylammonium chloride, bromide or monoalkylsulfate and N-acylaminoethyl-N,N-diethyl-N-benzylammonium chloride, bromide or monoalkyl sulfate, where acyl is preferably stearyl or oleyl.

Examples of suitable nonionic surfactants which can be used as detergent substances are fatty alcohol ethoxylates (alkylpolyethylene glycols); alkylphenol polyethylene glycols; alkyl mercaptan polyethylene glycols; fattyamine ethoxylates (alkylaminopolyethylene glycols); fatty acid ethoxylates (acylpolyethylene glycols); polypropylene glycol ethoxylates (Pluronic); fatty acid alkylolamides (fatty acid amide polyethylene glycols); sucrose esters; sorbitol esters and polyglycol ether.

Examples of amphoteric surfactants which can be added to the shampoos are N—($C_{12}$-$C_{18}$-alkyl)-.beta.-aminopropionates and N—($C_{12}$-$C_{18}$-alkyl)-.beta.-iminodipropionates as alkali metal and mono-, di- and trialkylammonium salts; N-acylamidoalkyl-N,N-dimethylacetobetaine, preferably N—($C_8$-$C_{18}$-acyl)amidopropyl-N, N-dimethylacetobetaine; $C_{12}$-$C_{18}$-alkyldimethylsulfopropylbetaine; amphoteric surfactants based on imidazoline (commercial name: Miranol®, Steinapon®, preferably the sodium salt of 1-(β-carboxymethyloxyethyl)-1-(carboxymethyl)-2-laurylimidazolinium; amine oxide, for example $C_{12}$-$C_{18}$-alkyldimethylamine oxide, fatty acid amidoalkyldimethylamine oxide.

The hair care preparations according to the invention can additionally contain further additives customary in hair care such as for example perfumes, colorants, also those which simultaneously dye or tint the hair, solvents, opacifying agents and pearly luster agents, for example esters of fatty acids with polyols, magnesium and zinc salts of fatty acids, dispersions based on copolymers, thickening agents such as sodium, potassium and ammonium chloride, sodium sulfate, fatty acid alkylolamides, cellulose derivatives, natural rubbers, also plant extracts, protein derivatives such as gelatin, collagen hydrolysates, polypeptides with a natural or synthetic basis, egg yolk, lecithin, lanolin and lanolin derivatives, fats, oils, fatty alcohols, silicones, deodorizing agents, substances with antimicrobial activity, substances with anti-seborrhoeic activity, substances with keratolytic and keratoplastic effect, such as, for example, sulfur, salicylic acid and enzymes as well as further anti-dandruff agents such as olamine, climbazol, zink pyrithion, ketoconazole, salicylic acid, sulfur, tar preparations, derivatives of undecenic acid, extracts of nettel, rosmary, cottonwood, birch, walnut, willow bark and/or arnica.

As the compositions according to the present invention are particularly suitable to treat dandruff, the present invention also relates to a method of treating the scalp, said method comprising the steps of contacting the scalp with a hair care preparation comprising erythrulose and a caprylate, preferably glyceryl caprylate. In a preferred embodiment the method is directed to the treatment of dandruff. In another preferred embodiment, the hair care preparation is a rinse off composition in the form of a shampoo or a conditioner. In a further preferred embodiment, the method furthermore comprises the step of rinsing the hair with water.

The shampoos are produced in a manner known per se by mixing the individual components and where necessary further processing appropriate for the particular type of preparation.

Examples of hair care preparations in which the combination of erythrulose and hydroxacetophenone can be used according to the invention and which may be mentioned are hair conditioners, hair tonics and hair regenerating compositions, which are rinsed off from the hair after a certain time or, depending on the formulation, can also remain on the hair.

All these preparations are also produced as already mentioned for the shampoo in a manner known per se with the addition of the combination of erythrulose and hydroxacetophenone.

The following examples are provided to further illustrate the compositions and effects of the present invention. These examples are illustrative only and are not intended to limit the scope of the invention in any way.

EXAMPLE 1: SYNERGISTIC AFFECT AGAINST MICROBES

The antimicrobial efficacy is assessed in analogy to the regulatory challenge test method (NF EN ISO11930). Thus, solutions of the respective active(s) in ethanol are prepared and further dissolved in physiological serum with 0.85 wt.-% NaCl in the concentrations as outlined in table 1 under sterile conditions. The samples were solubilized in physiological serum supplemented with 1 wt.-% ethanol. A control was prepared under sterile condition based on a serum with 0.85 wt.-% NaCl and 1 wt.-% ethanol (C1).

The control as well as the solutions of the active(s) were deposed in 96-deep well plates (1.6 ml/well). The wells are contaminated resulting in the initial contamination as outlined in table 1. After the contamination, each well was thoroughly mixed to ensure a homogeneous distribution of bacteria. Then each plate was incubated at 22° C. for 24 h. The counting of the (remaining) population is carried out 24 h after contamination.

Protection Against Yeast

TABLE 1

Results 0.1% Erythrulose (corresponds to 0.08% active)

| Test solution | Time [h] | *Candida albicans* colony count [cfu/ml] | Log reduction |
|---|---|---|---|
| 0.1 wt.-% erythrulose | 0 | 25000 | |
| 0.2 wt.-% glyceryl caprylate | 24 | 100 | 2.4 |
| 0.2 wt.-% erythrulose | 0 | 25000 | |
| 0.1 wt.-% glyceryl caprylate | 24 | 1000 | 1.4 |
| C1 | 0 | 25000 | |
|  | 24 | 5500 | 0.5 |

As can be seen in the table above the combination of erythrulose and glyceryl caprylate shows a synergistic effect against *Candida albicans*. The combination of erythrulose <glyceryl caprylate performs best.

Protection Against Acne

TABLE 2

Results 0.1% Erythrulose (corresponds to 0.08% active)

| Test solution | Time [h] | *Propionibacterium acnes* colony count [cfu/ml] | Log reduction |
|---|---|---|---|
| 0.1 wt.-% erythrulose | 0 | 310000 | |
|  | 24 | 3300 | 2 |
| 0.2 wt.-% glyceryl caprylate | 0 | 310000 | |
|  | 24 | 260 | 3 |
| 0.1 wt.-% erythrulose 0.2 wt.-% glyceryl caprylate | 0 24 | 310000 0 | 5.5 |
| 0.3 wt.-% erythrulose | 0 24 | 310000 100 | 3.5 |
| 0.3 wt.-% glyceryl caprylate | 0 24 | 310000 10 | 4.5 |
| 0.2 wt.-% erythrulose 0.1 wt.-% glyceryl caprylate | 0 24 | 310000 26 | 4 |
| C1 | 0 24 | 310000 31000 | 1 |

As can be seen in the table above the combination of erythrulose and glyceryl caprylate shows a synergistic effect against *Propionibacterium acnes*. To reach germ-free conditions the combination of erythrulose <glyceryl caprylate performs best.

The invention claimed is:

1. A method of killing and/or inhibiting growth of *Candida albicans* and/or *Propionibacterium acnes*, wherein the method comprises contacting *Candida albicans* and/or *Propionibacterium acnes* with an antimicrobial composition comprising a mixture of erythrulose and glycerol caprylate in amounts effective to kill and/or inhibit growth of the *Candida albicans* and/or *Propionibacterium acnes*, wherein the mixture has a weight ratio (w/w) of the glycerol caprylate to the erythrulose of >1.

2. The method according to claim 1, wherein the weight ratio (w/w) of the caprylate to the erythrulose is 1.25 to 3.

3. The method according to claim 1, wherein the weight ratio(w/w) of the caprylate to the erythrulose is 1.5 to 2.5.

4. The method according to claim 1, wherein the erythrulose is present in an amount of about 0.01 to 3 wt. %, based on total weight of the composition.

5. The method according to claim 1, wherein the erythrulose is present in an amount of about 0.01 to 3 wt. %, based on total weight of the composition.

6. The method according to claim 1, wherein the erythrulose is present in an amount of about 0.025 to 2 wt. %, based on total weight of the composition.

7. The method according to claim 1, wherein the erythrulose is present in an amount of about 0.04 to 1 wt. %, based on total weight of the composition.

8. The method according to claim 1, wherein the erythrulose is present in an amount of about 0.04 to 0.75 wt. %, based on total weight of the composition.

9. The method according to claim 1, wherein the glyceryl caprylate is present in an amount of 0.1 to 2 wt. %, based on total weight of the composition.

10. The method according to claim 1, wherein the glyceryl caprylate is present in an amount of 0.2 to 1.5 wt. %, based on total weight of the composition.

11. The method according to claim 1, wherein the glyceryl caprylate is present in an amount of 0.3 to 1.0 wt. %, based on total weight of the composition.

12. The method according to claim 1, wherein the composition is a topical cosmetic or pharmaceutical composition.

13. The method according to claim 12, wherein the composition is a shampoo preparation, a hair conditioner, an O/W emulsion, a W/O emulsion or a gel.

14. The method according to claim 1, wherein the composition further comprises water and at least one agent selected from the group consisting of surfactants, emulsifiers, thickeners and oils.

* * * * *